United States Patent [19]

Kesling, Jr. et al.

[11] 4,189,599
[45] Feb. 19, 1980

[54] PREPARATION OF DIMETHYL ADIPATE BY THE HYDROGENATION OF DIMETHYL HEX-3-ENDIOATE

[75] Inventors: Haven S. Kesling, Jr., Drexel Hill, Pa.; Lee R. Zehner, Dublin, Ohio

[73] Assignee: Atlantic Richfield Company, Los Angeles, Calif.

[21] Appl. No.: 963,531

[22] Filed: Nov. 24, 1978

Related U.S. Application Data

[63] Continuation-in-part of Ser. No. 898,235, Apr. 20, 1978, abandoned.

[51] Int. Cl.$^2$ ............................................. C07C 69/44
[52] U.S. Cl. ........................................ 560/190; 560/204
[58] Field of Search .................. 560/190, 204; 562/592

[56] References Cited

U.S. PATENT DOCUMENTS

| | | | |
|---|---|---|---|
| 3,725,489 | 4/1973 | Fuhrmann et al. | 560/190 |
| 3,737,395 | 6/1973 | Arnold et al. | 562/592 |
| 3,755,194 | 8/1973 | Avilov et al. | 560/190 |

FOREIGN PATENT DOCUMENTS 50-130714  10/1975  Japan .

OTHER PUBLICATIONS

Carraro, Giorgi et al., "Adipic Acid from 1,3-Butadiene," German Offen. No. 1,904,429 (see Chemical Abstracts, vol. 72, 1970 #12118u).

*Primary Examiner*—James O. Thomas, Jr.
*Assistant Examiner*—L. Hendriksen
*Attorney, Agent, or Firm*—Delbert E. McCaslin

[57] ABSTRACT

A process for the preparation of dimethyl adipate by the hydrogenation of dimethyl hex-3-endioate, having the formula $CH_3O_2CCH_2CH=CHCH_2CO_2CH_3$, derived from the oxidative carbonylation of 1,3-butadiene with a mixture of carbon monoxide and oxygen at a temperature of from 60° C. to 200° C. and pressures of from 15 psig to 5000 psig in the presence of a catalytic mixture of a platinum group metal compound and a copper or iron oxidant salt compound with at least a stoichiometric amount of a dehydrating agent, which comprises subjecting the dimethyl hex-3-endioate to a liquid phase hydrogenation at temperatures of from about ambient to about 150° C. under hydrogen pressures of from about 10 psig to 1000 psig in the presence of an effective amount of a hydrogenation catalyst to produce dimethyl adipate, and recovering the dimethyl adipate.

13 Claims, No Drawings

PREPARATION OF DIMETHYL ADIPATE BY THE HYDROGENATION OF DIMETHYL HEX-3-ENDIOATE

CROSS REFERENCE TO RELATED APPLICATIONS

This application is a continuation-in-part application of co-pending application Ser. No. 898,235, filed Apr. 20, 1978, entitled INTEGRATED PROCESS FOR THE PREPARATION OF ADIPIC ACID FROM 1,3-BUTADIENE and now abandoned.

BACKGROUND OF THE INVENTION

This application is related to co-pending application Ser. No. 808,939, filed June 22, 1977, in the names of Haven S. Kesling, Jr. and Lee R. Zehner, entitled PREPARATION OF UNSATURATED DIESTERS BY CATALYTIC OXIDATIVE CARBONYLATION OF DIOLEFINS, which application discloses certain aspects of the present invention.

In the above-co-pending application of Kesling and Zehner, which application is incorporated herein by reference, there is disclosed a process for the preparation of unsaturated diesters in general by oxidatively carbonylating with carbon monoxide and oxygen or an oxygen-containing gas in the presence of a platinum group metal catalyst compound, a copper or iron oxidant salt compound and a stoichiometric amount of a dehydrating agent at a pressure of between about 15 psig and 5000 psig and a temperature in the range of about 25° C. to 200° C., and alternatively contemplates the use of catalytic quantities of alcohols and ligands.

The present invention is directed to hydrogenation of the diester, dimethyl hex-3-endioate derived from the oxidative carbonylation of the diolefin, 1,3-butadiene, as disclosed in the above Kesling and Zehner application, and the conversion of the unsaturated diester to dimethyl adipate which dimethyl adipate may be hydrolyzed to adipic acid having a high degree of purity without resorting to the involved recrystallization procedures associated with prior art processes used to free adipic acid from various impurities especially if the adipic acid is to be employed to produce Nylon 66. The unsaturated diester, dimethyl hex-3-endioate, the adipic acid precursor, or the dimethyl adipate after hydrogenation of the diester may be distilled to remove impurities providing a more economical and efficient method for the preparation of high grade adipic acid by hydrolysis.

While oxidative carbonylation and hydrogenation as well as acid-catalyzed hydrolysis reactions are generally known, the prior art does not shown or describe a process for the oxidative carbonylation of 1,3-butadiene to prepare dimethyl hex-3-endioate and the catalytic hydrogenation thereof to dimethyl adipate, which may itself be employed as a plasticizer or lubricant.

A recent Japanese Kokai No. 75-130,714, Oct. 16, 1975, describes the preparation of carboxylic acid esters by reacting conjugated dienes, carbon monoxide and at least stoichiometric amounts and generally an excess of a monohydric alcohol in the presence of molecular oxygen and a Group 8 noble metal catalyst. Dehydrating agents may be used if necessary to maintain non-aqueous conditions. Very small amounts of the dimethyl hex-3-endioate are produced.

SUMMARY OF THE INVENTION

This invention relates to the preparation of dimethyl adipate by the hydrogenation of dimethyl hex-3-endioate derived from the catalytic oxidative carbonylation of 1,3-butadiene with carbon monoxide and oxygen with at least stoichiometric quantities of a dehydrating agent selected from acetals, ketals, carboxylic ortho esters, trialkylorthoborates or dialkoxycycloalkanes.

In the aforementioned application of Haven S. Kesling and Lee R. Zehner unsaturated diesters, which include the diester, dimethyl hex-3-endioate, are prepared by the oxidative carbonylation of the diolefin, 1,3-butadiene, with carbon monoxide and oxygen in the presence of a platinum group metal compound, a copper or iron oxidant salt compound and a stoichiometric quantity of the dehydrating agent and alternatively, a catalytic quantity of an alcohol and various ligands. The dimethyl hex-3-endioate produced is further processed by the method of the present invention to prepare dimethyl adipate.

It is a primary object of this invention therefore, to provide a method for preparation of dimethyl adipate in high purity, conversion and yield via the oxidative carbonylation of 1,3-butadiene and hydrogenation of the resulting unsaturated dimethyl hex-3-endioate to dimethyl adipate.

It is another object of this invention to provide a novel reaction sequence for the ultimate conversion of carbon monoxide, oxygen and 1,3-butadiene to dimethyl adipate.

It is a further object of this invention to provide a series of specific catalytic and operational reaction mechanisms for the preparation of dimethyl adipate which may be hydrolyzed to adipic acid having high purity.

These and other objects and advantages of this invention will become apparent from the description of the invention which follows and from the claims.

DETAILED DESCRIPTION OF THE INVENTION

In order to carry out the process of this invention, the unsaturated diester, dimethyl hex-3-endioate, having the formula $CH_3O_2CCH_2CH=CHCH_2CO_2CH_3$ is produced by reacting, under liquid phase conditions, a mixture of carbon monoxide and oxygen or an oxygen-containing gas and at least a stoichiometric amount of a dehydrating agent selected from acetals, ketals, carboxylic ortho esters, trialkylorthoborates or dialkoxycycloalkanes with butadiene at elevated temperatures and pressures in the presence of a catalytic mixture of a platinum group metal compound or mixtures thereof and a copper (I), copper (II), iron (II) or iron (III) oxidant salt compound, and alternatively a catalytic quantity of an organic mono- or poly-dentate ligand or coordination complex compound, selected from the group consisting of alkyl, aryl, and halogen substituted phosphines, arsines, stibines and alkali metal salts, and catalytic quantities of a monohydric saturated aliphatic, alicyclic or aralkyl alcohol containing from 1 to 20 carbon atoms which may contain other substituents which do not interfere with the reaction.

To place this invention in its proper context, the overall oxidative carbonylation reaction for the preparation of the unsaturated diester, dimethyl hex-3-endioate, indicated above and as set forth in the aforementioned co-pending application of Haven S. Kesling and Lee R. Zehner, Ser. No. 808,939, filed June 22, 1977, involving the oxidative carbonylation of 1,3-butadiene will also be described and the inter-relation between the oxidative carbonylation and hydrogenation of the diester to produce dimethyl adipate will be pointed out.

The oxidative carbonylation reaction between the 1,3-butadiene, carbon monoxide, oxygen, dehydrating agent, catalyst, etc. may be carried out in an autoclave or any other appropriate reactor. Although the order of addition of reactants and catalyst components may vary, a general procedure is to charge the 1,3-butadiene, dehydrating agent, platinum group metal compound and oxidant salt compound into the reaction vessel, and if desired a ligand or coordination complex compound and a catalytic quantity of an alcohol, then introduce the proper amount of carbon monoxide and oxygen to the desired reaction pressure and then heat the mixture to the desired temperature for the appropriate period. The addition of the oxygen or oxygen-containing gas, such as air, can be a pulsed or continuous addition to the reaction system. The reaction products are recovered and treated by any conventional method such as distillation and/or filtration, etc. to effect separation of the dimethyl hex-3-endioate diester from unreacted materials, platinum group metal salt compound, oxidant salt compound and other by products. Catalysts, including solvents which may have been employed, may be recycled to the system.

The 1,3-butadiene may be employed in concentrations of from about 10 to 80 weight percent, preferably 20 to 60 weight percent, or on a mole per mole basis with the acetal, ketal, carboxylic ortho ester, trialkylorthoborate or dialkoxycycloalkane employed.

The dehydrating agents employed as reactants in the preparation of dimethyl hex-3-endioate and in at least stoichiometric amounts in the oxidative carbonylation process of the invention include acetals, ketals, carboxylic ortho esters, trialkylorthoborates, and dialkoxycycloalkanes.

The acetals and ketals suitable for use in the process of the present invention conform to the general formulae:

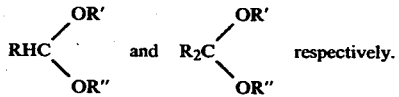 respectively.

R may be a substituted or unsubstituted alkyl group containing from 1 to 20 carbon atoms preferably 1 to 10 carbon atoms. R may also be a substituted or unsubstituted alicyclic, or an aryl group containing one or more benzenoid rings preferably not more than 3 rings which may be fused or joined by single valency bonds. R' and R'' which may be the same or different may be a substituted or unsubstituted alkyl group containing from 1 to 8 carbon atoms preferably 1 to 4 carbon atoms in the alkyl chain or an aralkyl group containing 6 carbon atoms in the ring and from 1 to 4 carbon atoms in the alkyl substituent. R, R' and R'' may contain substituents such as amido, alkoxy, amino, carboxy, cyano, etc. radicals. Representative acetals suitable for use in this invention include, for example, the 1,1-dialkoxyalkanes such as dimethoxymethane, dibutoxymethane, 1,1-dimethoxyethane, 1,1-dimethoxypropane, ethyl diethoxyacetate, 1,1,2-trimethoxyethane, 1,1-dimethoxy-2-propene, and dimethoxy- and diethoxy-phenylmethane, etc. In a like manner for example the acetals 1-methoxy-, 1-ethoxy- and 1-propoxytetrahydrofuran, 2,5-diethoxytetrahydrofuran, and 2-ethoxy-4-methyl-3,4-dihydro-2H-pyran etc. may be employed. Representative ketals suitable for use in this invention include for example, 2,2-dimethoxy-, 2,2-diethoxy- and 2,2-dipropoxy-propane, butane, pentane, etc. 3,3-dimethoxy- and 3,3-diethoxy-1-pentene, 1-butene, etc., 1,1-dimethoxycyclohexane, 1,1-diethoxycyclohexane, 1,1-dibutoxycyclohexane, etc., 1,1-dibutoxy-4-methylcyclohexane, 1,1-dimethoxy-1,2,3,4-tetrahydronaphthalene, etc. and 1,1-bis(2-propenoxy)cyclohexane.

The carboxylic ortho esters suitable for use in the process of the invention conform to the general formula

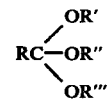

wherein R may be a hydrogen or a substituted or unsubstituted alkyl group containing from 1 to 20 carbon atoms preferably 1 to 10 carbon atoms. R may also be an alicyclic, or an aryl group containing one or more benzenoid rings preferably not more than 3 rings which may be fused or joined by single valency bonds. R', R'' and R''' which may be the same or different may be substituted or unsubstituted alkyl groups containing from 1 to 8 carbon atoms preferably 1 to 4 carbon atoms in the alkyl chain or an aralkyl group containing 6 carbon atoms in the ring and from 1 to 4 carbon atoms in the alkyl substituent. R, R', R'', and R''' may contain substituents such as amido, alkoxy, amino, carboxy, cyano, etc. Representative carboxylic ortho esters suitable for use in this invention include, for example trimethyl orthoformate, triethyl orthoformate, triphenyl orthoformate, tri-n-propyl orthoformate, etc., triethyl, tripropyl, tributyl, trimethyl orthoacetate, etc., trimethyl, triethyl, tripropyl, tributylorthopropionate, etc., trimethyl, triethyl, tripropyl, tributyl orthobutyrate, etc., trimethyl, triethyl, tripropyl, tributyl, orthoisobutyrate, etc., trimethyl, triethyl, tripropyl, tributyl orthocyanoacetate, etc., trimethyl, triethyl, tripropyl, tributyl orthophenylacetate, etc., trimethyl, triethyl, tripropyl, tributyl ortho-α-chloroacetate, etc., trimethyl, triethyl, tripropyl, tributyl ortho-α-bromoacetate, etc., trimethyl, triethyl, tripropyl, tributyl orthobenzoate, etc., trimethyl, triethyl, tripropyl, tributyl, ortho-p-chlorobenzoate, etc., hexamethyl-p-diorthophthalate, etc., ethyl triethoxyacetate, hexaethyl orthooxalate, triethyl ortho-3-butynoate, etc. In a like manner the esters trimethyl, triethyl, tripropyl orthocarbonate, 2-isopropyl-2-methoxy-1,3-dioxolane, 2-methyl-2-ethoxy-1,3-dioxolane, 2,2-diethoxytetrahydrofuran, 2,2-diethoxychroman, 1,4,5-trioxaspiro[4,4-]nonane, 2,6,7-trioxabicyclo[2,2,2]octanes, 2,4,10-trioxaadamantane-2,4,10-trioxatricyclo[3,3,1,13,7]decane may be employed.

The orthoborate esters employed in at least stoichiometric quantities and suitable for use in the process of the present invention are preferably symmetrical and conform to the general formula

wherein R' is a substituted or unsubstituted alkyl group containing from 1 to 8 carbon atoms in the alkyl chain or an aralkyl group containing 6 carbon atoms in the ring and from 1 to 4 carbon atoms in the alkyl substituent. Particularly preferred are the orthoborates wherein each R' is a straight chain alkyl group containing from 1 to 4 carbon atoms such as triethyl borate. Representative ortho borate esters suitable for use in this invention include, for example, trimethylborate, triethylborate, tri-2-chloroethyl borate, tritolyl borates, tri-methoxybenzyl borates, tri-chlorobenzyl borates, tri-benzyl borate, tri-4-butylphenyl borate, tri-n-propyl and tri-isopropyl borates, tri-(1,3-dichloro-2-propyl) borate, tri-n-butyl, tri-s-butyl and tri-t-butyl borates, tri-(β,β,β-trichloro-t-butyl)borate, triphenyl borate, tri-o-chlorophenyl borate, tri-n-amyl borate, tri-t-amyl borate, tri-(o-phenylphenyl) borate, tri-n-hexyl borate, tri-3-heptyl borate, tri-3-pentyl borate, tri-n-octyl and tri-isooctyl borates, tri-(2-ethylhexyl)borate, tri-(methylisobutylcarbonyl) borate, tri(diisobutylcarbinyl) borate, tri-(2,5-dimethylbenzyl) borate, etc.

The dialkoxycycloalkanes, which are the preferred dehydrating agents for use in the present invention, in at least stoichiometric quantities, conform to the general formula

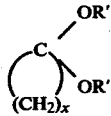

wherein R' is a substituted or unsubstituted alkyl group containing from 1 to 4 carbon atoms and x is an integer of from 4 to 9. R' may contain substituents such as amido, alkoxy, amino, carboxy, cyano, etc. radicals. In addition, the cyclic ring may be substituted with alkyl groups of up to 4 carbon atoms. Dimethoxycyclohexane is the most preferred. Representative dialkoxycycloalkanes include for example, dimethoxy-, diethoxy-, dipropoxy- and dibutoxycyclopentanes, and the corresponding dimethoxy, diethoxy, dipropoxy and dibutoxycyclohexanes, heptanes, octanes, nonanes and decanes, as well as 4-ethyl-1,1-dimethoxycyclohexane, etc.

The dialkoxycycloalkanes are the most preferred reactant dehydrating agent compounds for use in the oxidative carbonylation reaction to prepare the dimethyl hex-3-endioate, especially 1,1-dimethoxycyclohexane, which dehydrating agents are essentially converted to ketones during the reaction. These ketones may be conveniently regenerated to the dialkoxycycloalkanes at temperatures of from −35° C. to 60° C. preferably −10° C. to 25° C. in the presence of an aliphatic alcohol, with the alcohol corresponding to the alkyl substituent of the original alkoxy group of the cycloalkane, and a strongly acidic sulfonated polyaromatic ion exchange resin (sold, for example, commercially as "Amberlyst 15" by Rohm and Haas Co.) and having a bulk density of approximately 595 g/l., a hydrogen ion concentration of approximately 4.9 milliequivalents/g. dry, a surface area of from about 40 to 50 m²/g. and an average pore diameter of from about 200 to 600 Angstrom units, or acid zeolites followed by a neutralization with a base such as triethylamine, pyridine, alkaline earth and alkali metal salt compounds, e.g., calcium and sodium carbonate and hydroxide, quaternary ammonium salt compounds as well as basic ion exchange resins, to fix the ketone/dialkoxycycloalkane equilibrium, and separation by azeotropic distillation.

A general postulated equation for the reaction using dimethoxycyclohexane in the oxidative carbonylation of 1,3-butadiene may be represented as follows:

$CH_2=CH-CH=CH_2 + 2CO + \frac{1}{2}O_2 +$
(butadiene)

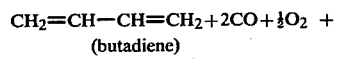

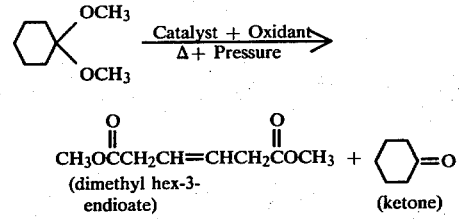

Regeneration of the dimethoxycyclohexane which was converted to the ketone, cyclohexanone may be represented as follows:

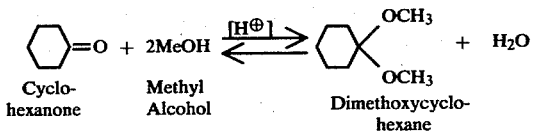

The platinum group metal compounds which may be employed as catalysts in the oxidative carbonylation of 1,3-butadiene are the palladium, platinum, rhodium, ruthenium, iridium, and osmium salts or mixtures thereof. The chemical forms of the platinum group metal salt compounds which can be used as such or as mixtures or formed in the reaction system from the metals per se are, for example, the palladium, platinum, rhodium, ruthenium, iridium and osmium, halides, sulfates, nitrates, oxides, oxalates, acetates and trifluroacetates, preferably the palladium (II) halides, particularly palladium (II) chloride. Representative catalytic platinum group metal salt compounds include, for example palladium (II) chloride, platinum (II) chloride, rhodium (III) chloride, ruthenium (III) chloride, palladium (II) sulfate, palladium (II) acetate, palladium (II) trifluroacetate, palladium (II) iodide, rhodium (III) bromide, iridium (III) chloride, platinum (II) sulfate, osmium (II) chloride, palladium (II) oxide, osmium tetroxide, iridium (III) sulfate, etc. As indicated above the metals as such may be added to the reaction as part of the catalyst mixture, the salt compound being formed in situ from at least a portion of the platinum group metal under reaction conditions.

The palladium, platinum, rhodium, ruthenium, osmium and iridium compounds employed may be in a homogeneous state in the reaction mixture at reaction conditions. Thus, the compounds may be present in solution, or suspension and may also be on support materials such as alumina, silica gel, aluminosilicates, activated carbon or zeolites or may be anchored to a polymer support. The compounds may be partially or completely soluble under reaction conditions. The oxidative carbonylation of 1,3-butadiene is generally carried out in the presence of a catalytic proportion of the platinum group metal salt compound and will proceed with small amounts of the metal salt compounds hereinabove described. Generally the proportions of the platinum group metal salt compound used in the reaction will be equivalent to between about 0.001 to 5 weight percent of the 1,3-butadiene employed and are preferably employed in amounts between about 0.01 to 2 percent by weight of the 1,3-butadiene employed. Larger or smaller amounts may be employed at varied pressures and temperatures.

As mentioned hereinabove, alternatively, a ligand or coordination complex compound of the platinum group metal salt compound may be employed in the oxidative carbonylation process of the invention as co-catalyst in the catalytic mixture and thereby also achieve a pronounced increase in the selectivity for the unsaturated diester, dimethyl hex-3-endioate. The ligands may be, for example, alkyl or aryl phosphines, arsines, or stibines or salts of the alkali metals, e.g., lithium, sodium, potassium, rubidium, cesium salts, such as lithium iodide, sodium chloride, potassium bromide, lithium acetate, lithium chloride, etc. The complexes of the metal salt compounds which are suitable for use in the process of the present invention include complex compounds of palladium, platinum, rhodium, ruthenium, osmium and iridium. The complex compounds may contain one or more atoms of the salt metals in the molecule and when more than one such atom is present, the metals may be the same or different. The mono- or polydentate ligands which are present in the molecule of the complex compounds and in which at least one of the electron-donating atoms is an atom of phosphorous, arsenic or antimony or a halide ion containing a lone pair of electrons may be, for example, organo-phosphines, -arsines and -stibines. Suitable monodentate ligands include alkyl phosphines such as trimethylphosphine and tributylphosphine, aryl-phosphines such as diethylphenylphosphine and radicals derived from such phosphines, for example the radical having the formula $-P(CH_3)_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. It is preferred to employ the alkali metal halides, particularly the lithium halides such as lithium chloride and lithium iodide.

Benzonitrile, acetonitrile, isocyanates, isothiocyanates, pyridine, pyridyls, pyrimidine, quinoline, isoquinoline may also serve as suitable ligands to modify the platinum group metal catalyst activity or catalyst solubility.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen, and halogen atoms; groups which may be bonded to the metal include, for example hydrocarbyl, hydrocarbyloxy, carbonyl, nitrosyl, cyano and $SnCl_3$—groups; molecules which may be bonded to the metal include, for example organic isocyanides and isothiocyanates. Examples of suitable complex compounds are those represented by the following formulae:

| | |
|---|---|
| $RhBr_3(PPhEt_2)_3$ | $Rh(CO)Cl(AsEt_3)_2$ |
| $RhCl(CO)(PPhEt_2)_2$ | $RhCl(CO)(PEt_3)_2$ |
| $Rh(Ph_2PCH_2CH_2PPh_2)_2Cl$ | $PdCl_2(PPh_3)_2$ |
| $Rh[(PhO)_3P]_3Cl$ | $PdI_2(PPh_3)_2$ |
| $Li_2PdI_4$ | $PtCl_2(p\text{-}ClC_6H_4PBu_2)_2$ |
| $(PhCN)_2PdCl_2$ | |

The complex compounds employed may be introduced into the reaction mixture as such, or they may be formed in situ from a suitable platinum group metal or metal compound noted above and the desired ligand.

The ligand or complex compounds may be used in catalytic amounts of from 0 to 3 percent preferably from 0.1 to 1 percent by weight of the 1,3-butadiene to be reacted although larger or smaller amounts may be employed at varied pressures or reaction rates.

The oxidant salt compounds which may be employed in an essentially anhydrous condition in the oxidative carbonylation of 1,3-butadiene and in catalytic amounts of from 0.1 to 10 weight percent preferably 0.50 to 6 weight percent include the iron (II), iron (III), copper (I) and copper (II) salts such as the halides, sulfates, trifluoroacetates, nitrates, oxalates, naphthanates, hex-3-endioates or acetates and preferably copper (II) chloride and iron (II) chloride. Representative oxidant salts include, for example copper (II) sulfate, copper (II) trifluoroacetate, copper (II) acetate, copper (II) oxalate, copper (II) triflate, copper (II) fluorosulfonate, copper (I) chloride, copper (I) sulfate, iron (III) sulfate, iron (II) iodide, iron (II) chloride, iron (III) acetate, iron (III) oxalate, copper (II) hex-3-endioate, iron (II) hex-3-endioate and iron (III) trifluoroacetate.

While not necessary to the oxidative carbonylation reaction, it is often desirable to add a small amount of an acid to aid in initiating the reoxidation (by oxygen) of copper (II) to copper (II) or iron (II) to iron (III). Suitable acids include for example hydrochloric, hydrobromic, sulfuric, phosphoric and acetic in concentrations of from 0–2 weight percent of 1,3-butadiene.

As indicated hereinabove, an alcohol in catalytic quantities may be employed in the oxidative carbonylation of the butadiene primarily to aid in initiating the oxidative carbonylation reaction and increase the solubility of the catalyst components. The alcohols may be employed in concentrations of from 0 to 20 and preferably 0.5 to 10 weight percent of the 1,3-butadiene employed. The alcohols may be saturated monohydric primary, secondary or tertiary alcohols and conform to the general formula ROH, wherein R is an optionally substituted aliphatic or alicyclic group containing from 1 to 20 carbon atoms and preferably the unsubstituted aliphatic alcohols containing from 1 to 8 carbon atoms. R may also be a substituted or an unsubstituted aralkyl group. In general, the substituents which may be amido, alkoxy, amino, carboxy, etc. radicals, in addition to the hydroxyl group, do not interfere with the reaction of the invention. Representative alcohols especially suitable for use in this invention are saturated monohydric alcohols such as methyl, ethyl, n-, iso-, sec-, and tert-butyl, amyl, hexyl, octyl, lauryl, n- and isopropyl, cetyl, benzyl, chlorobenzyl and methoxybenzyl alcohols as well as, for example, tolylcarbinol, cyclohexanol, heptanols, decanols, undecanols, 2-ethyl hexanol, nonanol, myristyl alcohol, stearyl alcohol, methyl cyclohexanol, pentadecanol, oleyl and eicosonyl alcohols, and the like.

The preferred alcohols are the primary and secondary monohydric saturated aliphatic alcohols such as methanol, ethanol, 1- and 2-propanol, n-butyl alcohol, etc., up to 8 carbon atoms. The R group of the alcohol may be different from the R', R" or R"' of the dehydrating agents noted hereinabove, resulting in the preparation of mixed diesters.

Solvents if desired, which are chemically inert to the reaction system may be employed, and are especially suitable in the oxidative carbonylation of 1,3-butadiene, and will generally improve the selectivity and conversion to the dimethyl hex-3-endioate as well as the catalyst solubility or boiling point range for product and catalyst recovery. Suitable solvents include for example, dioxane, dimethylcarbonate, dimethyladipate, benzene, nitrobenzene, acetonitrile, tetrahydrofuran, methyl acetate, ethyl acetate, isopropyl acetate, n-propyl formate, butyl acetates, cyclohexyl acetate, n-propyl benzoate, lower alkyl phthalates, etc. the alkyl sulfones and sulfoxides such as propyl ethyl sulfoxide, diisopropyl sulfone, diisooctyl sulfoxide, acetone, cyclohexanone, methyl formate, etc.

The oxidative carbonylation of 1,3-butadiene can be suitably performed by introducing the oxygen and carbon monoxide at a desired pressure into contact with the butadiene, dehydrating agent, the platinum group metal salt compound and the copper or iron oxidant salt and possibly a catalytic amount of an alcohol as well as a co-catalytic amount of a ligand or coordination complex and heating to the desired temperature. In general, a carbon monoxide pressure of about 15 psig to about 5000 psig partial pressure and preferably from 500 psig to about 2500 psig is employed. Stoichiometric quantities of carbon monoxide are generally employed. However, an excess of carbon monoxide may be employed, for example, in continuous processes where a large excess of or high carbon monoxide requirements are generally utilized, a suitable recycle of the unreacted carbon monoxide may be employed. The oxidative carbonylation of the butadiene will proceed at temperatures of from about 60° C. to 200° C. It is generally preferred to operate the process at temperatures in the range of 95° C. to 120° C. to obtain a convenient rate of reaction. Lower temperatures may be employed but the reaction rate is slower. Heating and/or cooling means may be employed interior and/or exterior of the reaction to maintain the temperature within the desired range.

At least stoichiometric amounts of oxygen or an oxygen-containing gas such as air may be employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent.

The oxidative carbonylation reaction time is generally dependent upon the temperature, pressure and on the amount and type of catalyst, oxidant and dehydrating agent being charged as well as the type of equipment being employed. Reaction times will vary dependent on whether the process is continuous or batch. The reaction time for butadiene is generally about 120 minutes.

After preparation of the desired diester, dimethyl hex-3-endioate (dimethyl adipate precursor), unreacted 1,3-butadiene and any alcohol employed may be separated from the reaction mixture by low temperature flash vacuum evaporation and the spent dehydrating agent, for example, which is now cyclohexanone, separated by distillation for regeneration and reuse. The catalyst components may be recycled as a slurry or any heavy materials (such as higher esters) flashed off before recycle of the catalyst for reuse in oxidative carbonylation.

EXAMPLE 1 — OXIDATIVE CARBONYLATION OF 1,3-BUTADIENE TO PREPARE DIMETHYL HEX-3-ENDIOATE 1,3-butadiene (1000 mmoles) along with 0.444 g. (2.5 mmole) palladium (II) chloride, 3.36 g. (25 mmole) copper (II) chloride and 0.21 g. (5 mmole) lithium chloride, 32 mmole of methyl alcohol and 1000 mmole of 1,1-dimethoxycyclohexane was reacted in a 500 ml nickel-molybdenum (Hastelloy alloy) stirred autoclave to prepare a mixture of 41.80 g. (243 mmoles) of cis and trans dimethyl hex-3-endioate, at a trans to cis ratio of 3:1, and 2.04 g. (12 mmoles) of dimethyl hex-2,4-diendioate. The liquid feed and solid catalyst components were charged into the autoclave as homogeneous solutions. The 1,3-butadiene was charged into a sight glass and allowed to come to thermal equilibrium and then charged into the autoclave as a liquid under pressure. The reaction temperature was 100° C. and the total initial carbon monoxide pressure was 1600 psig. The reaction was initiated by a 100 psig charge of oxygen and 1000 psig line purging charge of carbon monoxide giving a total system pressure of 1800 psig. A strong exotherm and pressure drop of 150–200 psig over a course of 20 minutes was observed. The oxygen cycle was repeated five more times in increments of 50 psig oxygen and 100 psig carbon monoxide at intervals of 20 minutes during an autoclave residence period of 120 minutes. A total pressure drop of about 1000 psig was observed. The reaction was terminated before completion and cooled to ambient temperature and vented to ambient pressure. Solids were separated from liquids by vacuum filtration. The 1,3-butadiene conversion and selectivities to the dimethyl hex-3-endioate based on the butadiene was 55 percent and 74 mole percent respectively. The dimethyl hex-3-endioate was isolated from the oxidative carbonylation reaction mixture by fractional vacuum distillation and analyzed by gas liquid chromatography (Fraction b.p. 123° C. @ 9 mm Hg.) for use in a subsequent hydrogenation step to prepare dimethyl adipate. The prefraction (b.p. 67° C. @ 54 mm Hg) containing cyclohexanone, 1-methoxycyclohexene and minor amounts of unreacted 1,1-dimethoxycyclohexane was cycled to a regeneration step for subsequent use in further oxidative carbonylation reactions. The pot residue from the oxidative carbonylation reaction containing a very small amount of dimethyl hex-3-endioate product heal and a slurry containing approximately 99.9 percent of the original charged palladium (II) chloride/copper (II) chloride and lithium chloride carbonylation catalyst mixture was recycled for use in a subsequent second pass 1,3-butadiene oxidative carbonylation reaction.

Hydrogenation of the dimethyl hex-3-endioate to produce dimethyl adipate is carried out under liquid phase conditions at temperatures of from ambient to about 150° C. preferably from about 100° C. to 125° C. under hydrogen pressures of from 10 psig to 1000 psig preferably 50 psig to 250 psig. The reaction may be carried out in any suitable pressure reactor at the desired temperatures and hydrogen pressures in the presence of a suitable hydrogenation catalyst in the form of a fixed, fluidized or moving catalyst bed. Hydrogenation reactions are generally exothermic and cooling means may be employed interior and/or exterior of the reactor to control and maintain the temperature within the desired range. A preferred method of the present invention for controlling the temperature and removing the exothermic heat of reaction especially in a continuous process is to recycle part of the dimethyl adipate produced back to the hydrogenator. From 20 to 80 weight percent of the product dimethyl adipate may be recycled and preferably 50 to 60 weight percent while between 40 and 50 weight percent of the dimethyl adipate product is taken off and employed, for example to prepare adipic acid by hydrolysis. While the liquid dimethyl hex-3-endioate diester is preferably hydrogenated as such, solvents may be employed with the diester to moderate the reaction. Hydrogenation solvents which may be used are aliphatic alcohols such as methanol, ethanol, butanol, pentanol, octanol, etc., aliphatic hydrocarbons such as hexane, pentane, heptane, etc., cyclic and aromatic hydrocarbons such as cyclohexane, cycloheptane, xylene, benzene, etc., ethers such as diethyl and dibutyl ether, dioxane, tetrahydrofuran, etc.

In the hydrogenation of the dimethyl hex-3-endioate, the hydrogen is generally employed in an excess of the stoichiometric amount required to convert the diester to dimethyl adipate. Thus, the preferred molar ratio of hydrogen to dimethyl hex-3-endiote entering the reaction zone is generally 5:1. Higher or lower ratios of hydrogen to ester may be employed in the process provided the hydrogen is employed in at least the stoichiometric amount of 1:1.

The types of hydrogenation catalysts which may be employed in hydrogenation of the dimethyl hex-3-endiote have been extensively described in the prior art and any known hydrogenation catalyst, or mixture of catalysts, useful for the conversion of unsaturated esters to saturated esters may be used. Catalysts and the preparation thereof as described in U.S. Pat. Nos. 2,094,611, 2,201,235, and 3,374,184 and British Pat. Nos. 575,380, 1,151,567 and 1,181,137 may be used. In general heterogeneous catalysts comprising finely divided platinum, palladium, rhodium, ruthenium, cobalt and nickel which may be supported may be employed. Platinum oxides and palladium oxides, Raney nickel, platinum group metals on alumina or carbon may also be employed. Hydrogenation catalysts containing copper either in elemental form or combined with oxygen, as well as other hydrogenating metal oxides employed in conjunction with copper, supported or unsupported, may be used. Homogeneous hydrogenation catalysts may also be used, for example, sodium carbonate tris(-triphenylphosphine)rhodium chloride as described in British Pat. No. 1,181,137, hydrido tris(triphenylphosphine) ruthenium (II) chloride, tris(triphenylphosphine) ruthenium chloride and tripyridine rhodium (III) chloride.

A general postulated equation for the reaction may be represented as follows:

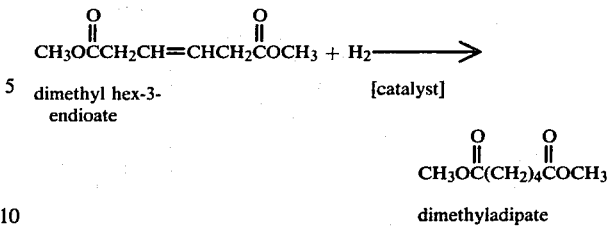
dimethyl hex-3-endioate dimethyladipate

The hydrogenation catalysts may be prepared by any of the convenient methods such as by precipitation or fusion as described in the above noted references. Many hydrogenation catalysts are commercially available.

EXAMPLE 2—HYDROGENATION

A mixture of 21.92 g. (127.5 mmoles) of dimethyl hex-3-endioate as prepared and isolated in Example 1 above was dissolved in 125 ml of absolute methanol and was hydrogenated in an internally cooled Paar hydrogenation apparatus at 50° C. under 200 psig hydrogenation pressure in the presence of 1.0 g. of 5 percent palladium on powdered activated carbon. The reaction was carried out for a period of ten minutes after which the pressure drop ceased. Gas liquid chromatographic analysis showed a 100 percent conversion of the dimethyl hex-3-endioate diester with 97 percent selectivity to dimethyl adipate. Straight distillation of the hydrogenation reaction product resulted in the isolation of 20.85 g. (119.9 mmoles) of pure dimethyl adipate (b.p. 100° C. @ 10 mm Hg.) representing a 94 percent isolated yield.

EXAMPLE 3—CONTINUOUS OXIDATIVE CARBONYLATION—HYDROGENATION PROCESS

A number of runs were carried out employing a solution of 1,1-dimethoxycyclohexane/cyclohexanone (100 g., 80/20 molar equilibrium mixture @ 10° C.—an equilibrium mixture of 1,1-dimethoxycyclohexane/cyclohexanone as was derived from regeneration of cyclohexanone and methanol to yield the dehydration agent 1,1-dimethoxycyclohexane as hereinafter described) charged into a stirred magnedrive 500 ml Hastelloy (nickel-molybdenum) autoclave along with sodium tetrachloropalladate (1.30 g., 4.1 mmoles) and copper (II) chloride (1.40 g., 10.4 mmole). 1.3-butadiene (100 ml) was charged into the autoclave as a liquid under pressure. The oxidative carbonylation reaction was carried out at 110° C. and 1800 psig total system pressure under continuous gas and liquid flow conditions. A carbon monoxide/air flow rate of 3 liters/minute was maintained for a four hour reaction period with a carbon monoxide to air ratio of 3:1. The entering gas stream contained 6-volume percent oxygen and the exiting gas stream contained 3.5 volume percent oxygen. 1,3-butadiene was fed into the reactor via a high pressure liquid feed pump at a rate of 100 ml/hour and the 1,1-dimethoxycyclohexane/cyclohexanone liquid feed was fed into the reactor at 100 ml/hr. The catalyst solution containing sodium tetrachloropalladate (0.41 moles/liter) and copper (II) chloride (1.04 moles/liter) in methanol was injected into the autoclave with a high pressure pump at a rate of 10 ml/hour along with the 80/20 molar equilibrium liquid feed mixture. As the oxidative carbonylation reaction is taking place the resulting reaction product mixture exited the reaction zone, it was stepped down to atmospheric pressure and was passed through a water-cooled condenser which was operating under a temperature gradient to control aerosol-formation from the autoclave. The product then passed into a gas-liquid separator where the unreacted butadiene, carbon monoxide, and air were recovered from the top of the separator for recycle (to the oxidative carbonylation reactor). The liquid product, dimethyl hex-3-endioate and some by products were then routed to a distillation train for separation and recovery for hydrogenation to dimethyl adipate.

Table 1 below indicates the reaction rates in mmoles of product/gram palladium/hour. Selectivity on both butadiene and carbon monoxide for these runs ranged between 80–85 mole percent.

TABLE 1

| Run No. | 1 | 2 | 3 | 4 | 5* | 6* |
|---|---|---|---|---|---|---|
| Temperature (°C.) | 105 | 110 | 115 | 120 | 105 | 110 |
| Rate (Total Product, mmole/gm. Pd. Hr.) | 820 | 1041 | 1128 | 1250 | 708 | 1050 |
| Rate (dimethylhex-3-endioate, mmole/gm. Pd. Hr.) | 670 | 818 | 868 | 800 | 640 | 830 |
| Rate (methyl pent-2,4-dienoate, mmole/gm. Pd. Hr.) | 112 | 145 | 188 | 200 | 98 | 147 |

*Ligand modified palladium catalyst di-μ-chlorodi-π-(dimethylhex-3-endioate)-dipalladium having the structural formula

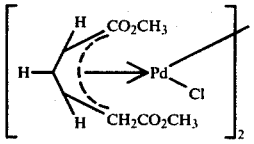

which has good solubility in the 1,1-dimethoxycyclohexane/cyclohexanone was used and was formed via reaction of sodium tetrochloropalladate and dimethylhex-3-endioate.

The liquid from the separator was processed through a series of fractionator columns. In the first column, the butadiene and some dissolved carbon dioxide are removed overhead, separated, and the butadiene recycled to the oxidative carbonylation reactor. Methanol and small amounts of other lights are also recovered, separated and the methanol recycled for use in regeneration of the dehydrating agent. The cyclohexanone, formed as a result of hydrolysis of the 1,1-dimethoxycyclohexane during reaction, is fractionated overhead from excess 1,1-dimethoxycyclohexane and by-products such as dimethyloxalate and methyl penta-2,4-dienoate. The cyclohexanone was sent to the regeneration column, and the non-selective lights which contain mostly methyl penta-2,4-dienoate, a small amount of methyl pentenoate, 1,1-dimethoxycyclohexane and a small amount of cyclohexanone were sent to a fixed catalyst bed hydrogenation reactor. The contained C5-unsaturated esters were hydrogenated to give methylvalerate, cyclohexanone, and 1,1-dimethoxycyclohexane. The mixture is separated by fractionation, and the methylvalerate further processed by an acid-catalyzed hydrolysis to recover valeric acid and methanol. The cyclohexanone and 1,1-dimethoxycyclohexane from this separation are also routed to regeneration. The final tower in the fraction train separates the dimethyl adipate precursor (dimethyl hex-3-endioate) and other non-selective by products (methyl nonadienoates and dimethyl decadiendioates) from the oxidative carbonylation catalyst components. The overhead materials upon hydrogenation give dimethyl adipate, small amounts of methylnonanoate, and small amounts of dimethyl sebacate.

The bottoms, containing oxidative carbonylation catalyst and heavies are partially flashed to purge the net make of heavies which may be used as fuel. The oxidative carbonylation catalyst slurry is picked up by the equilibrium mixture reaction solvent from regeneration and recycled to the oxidative carbonylation autoclave reactor. A portion of the catalyst bottoms is taken to a wiped film evaporator to recover spent catalyst for regeneration.

The methanol and cyclohexanone recovered in fractionation and hydrolysis processes are sent through a catalyst bed of strong acid sulfonated fluoropolymer (available commercially as NAFION and sold by DuPont). under the following conditions:

Methanol/cyclohexanone (molar): 4/1
Temperature (°C.): 10
Pressure (psig): 50
Liquid Hourly Space Velocity (hr$^{-1}$): 2
Cyclohexanone conversion (at equilibrium, %): 80

The resulting equilibrium mixture from the regeneration column was fractionated to remove excess methanol and water. The resulting 80:20 molar mixture of 1,1-dimethoxycyclohexane:cyclohexanone was sent to pick up the oxidative carbonylation catalyst slurry followed by routing to the oxycarbonylation autoclave reactor. Methanol was removed from the water and was returned to the regeneration column.

The dimethyl adipate precursor (dimethyl hex-3-endioate) and other non-selective by-products including small amounts of methyl nonadienoate and dimethyl decadiendioate were hydrogenated. The hydrogenation reactor consisted of a 5 percent palladium on powdered activated carbon fixed catalyst bed operated under the following conditions:

Hydrogen/dimethyl hex-3-endioate (molar): 2
Temperature (°C., Inlet): 50
Temperature (°C., Outlet): 150
Pressure (psig): 200
Weight Hourly Space Velocity (WHSV) (hours$^{-1}$, on fresh feed): 1.5
Recycle dimethyl adipate/fresh feed*: 2/1
* The hydrogenation exotherm was controlled by diluting the fresh feed with a circulating stream of dimethyl adipate.

The reactor effluent was flashed and unreacted hydrogen was recycled. The dimethyl adipate which was not recycled to hydrogenation reactor for exotherm control was sent to a fractionation column for separation and purification. The separation of dimethyl adipate from methyl nonanoate and dimethyl decadiendioate was made. The purified dimethyl adipate was hydrolyzed to adipic acid of excellent purity.

We claim:

1. A process for the preparation of dimethyl adipate by the hydrogenation of dimethyl hex-3-endioate, having the formula $CH_3O_2CCH_2CH=CHCH_2CO_2CH_3$, derived from the liquid phase oxidative carbonylation of 1,3-butadiene with a mixture of carbon monoxide and oxygen or an oxygen-containing gas and at least a stoichiometric amount of an acetal, ketal, carboxylic ortho ester, trialkylorthoborate or 1,1-dialkoxycycloalkane, at a temperature of from about 60° C. to 200° C. and pressures of from about 15 psig to about 5000 psig in the presence of a catalytic mixture of a platinum group metal compound or mixtures thereof and a copper (I), copper (II), iron (II) or iron (III) oxidant salt compound which comprises reacting under liquid phase conditions the dimethyl hex-3-endioate at a temperature of from about ambient to about 150° C. under a hydrogen pressure of from about 10 psig to 1000 psig in the presence of an effective amount of a hydrogenation catalyst to produce dimethyl adipate, and recovering said dimethyl adipate while at the same time recycling between about 20 weight percent and 80 weight percent of the dimethyl adipate produced by said hydrogenation of the dimethyl hex-3-endioate to the hydrogenator to control the temperature and remove the exothermic heat of reaction.

2. A process according to claim 1 wherein the oxidative carbonylation reaction is carried out in the presence of an alkali metal ligand compound and a catalytic amount of an aliphatic alcohol containing from 1 to 8 carbon atoms.

3. A process according to claim 1 wherein in the oxidative carbonylation reaction the dialkoxycycloalkane is 1,1-dimethoxycyclohexane, the platinum group metal compound is palladium (II) chloride, the oxidant salt compound is copper (II) chloride the reaction temperature is between about 95° C. and 120° C. and the pressure is from about 500 psig to 2500 psig.

4. A process according to claim 3 wherein the oxidative carbonylation is carried out in the presence of lithium chloride and a catalytic quantity of methyl alcohol.

5. A process according to claim 1 wherein the liquid phase hydrogenation of the dimethyl hex-3-endioate is carried out at a temperature of from about 100° C. to 125° C. at a pressure of from about 50 psig to 250 psig.

6. A process according to claim 1 wherein the hydrogenation catalyst is selected from the group consisting of platinum, palladium, rhodium, ruthenium, cobalt, nickel and copper-containing compounds.

7. A process according to claim 6 wherein the catalyst is supported.

8. A process according to claim 7 wherein the catalyst is palladium on activated carbon.

9. A process according to claim 1 wherein the hydrogenation is carried out in the presence of a solvent selected from the aliphatic alcohols, aliphatic, cyclic and aromatic hydrocarbons and ethers.

10. A process according to claim 9 wherein the solvent is methyl alcohol.

11. A process according to claim 1 wherein between about 50 and 60 weight percent dimethyl adipate is recycled.

12. A process according to claim 1 wherein the molar ratio of hydrogen to dimethyl hex-3-endioate entering the hydrogenator is 5:1.

13. A process according to claim 1 wherein the dehydrating agent is 1,1-dimethoxycyclohexane which is converted to cyclohexanone during the oxidative carbonylation reaction, said cyclohexanone being recovered and converted to 1,1-dimethoxycyclohexane at a temperature of from −10° C. to 10° C. in the presence of methyl alcohol and a strongly acidic sulfonated polyaromatic ion exchange resin followed by neutralization with a base to fix the cyclohexanone/1,1-dimethoxycyclohexane equilibrium.

* * * * *